US00PP30625P3

(12) United States Plant Patent
Olesen

(10) Patent No.: US PP30,625 P3
(45) Date of Patent: Jul. 2, 2019

(54) ROSE PLANT NAMED 'POULCAS051'

(50) Latin Name: ***Rosa* hybrid**
Varietal Denomination: Poulcas051

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 15/731,987

(22) Filed: Sep. 5, 2017

(65) Prior Publication Data

US 2019/0075702 P1 Mar. 7, 2019

(51) Int. Cl.
*A01H 5/02* (2018.01)
*A01H 6/74* (2018.01)

(52) U.S. Cl.
USPC ..... Plt./150
CPC ..... *A01H 6/749* (2018.05)

(58) Field of Classification Search
USPC ..... Plt./150
CPC ..... A01H 6/749; A01H 5/02
See application file for complete search history.

*Primary Examiner* — Keith O. Robinson

(57) ABSTRACT

A new garden rose plant of the Floribunda class which has abundant, red flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas051'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2009 and the resulting seeds were planted in a controlled environment in Fredensborg, Denmark. The new variety, named 'Poulcas051', originated as a single seedling from the stated cross.

The new variety may be distinguished from its male pollen parent and female seed parent primarily by the following characteristics. The male pollen parent plant has a growth height of 40 cm while the newly claimed plant grows to 65 cm in height. The female seed parent plant has pink flowers while the new variety has red flowers.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance.

This combination of qualities is not present in previously available commercial cultivars of this type, known to the inventor, and distinguish 'Poulcas051' from all other varieties of which we are aware.

As part of the rose development program, Mogens N. Olesen germinated the seeds from the aforementioned hybridization during winter of 2009 and conducted evaluations on the resulting seedlings in a controlled environment in Fredensborg, Denmark. 'Poulcas051' was selected in the spring of 2010 by the inventor as a single plant from the progeny of the aforementioned hybridization.

Asexual reproduction of 'Poulcas051' by rooted cuttings was first done by Mogens N. Olesen in the nursery in Fredensborg, Denmark in July, 2010. This initial and other subsequent asexual propagations conducted in controlled environments have demonstrated that the characteristics of 'Poulcas051' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas051'.

Specifically illustrated in FIG. 1 of the drawings are open flowers and flower petals detached.

Figure 1:
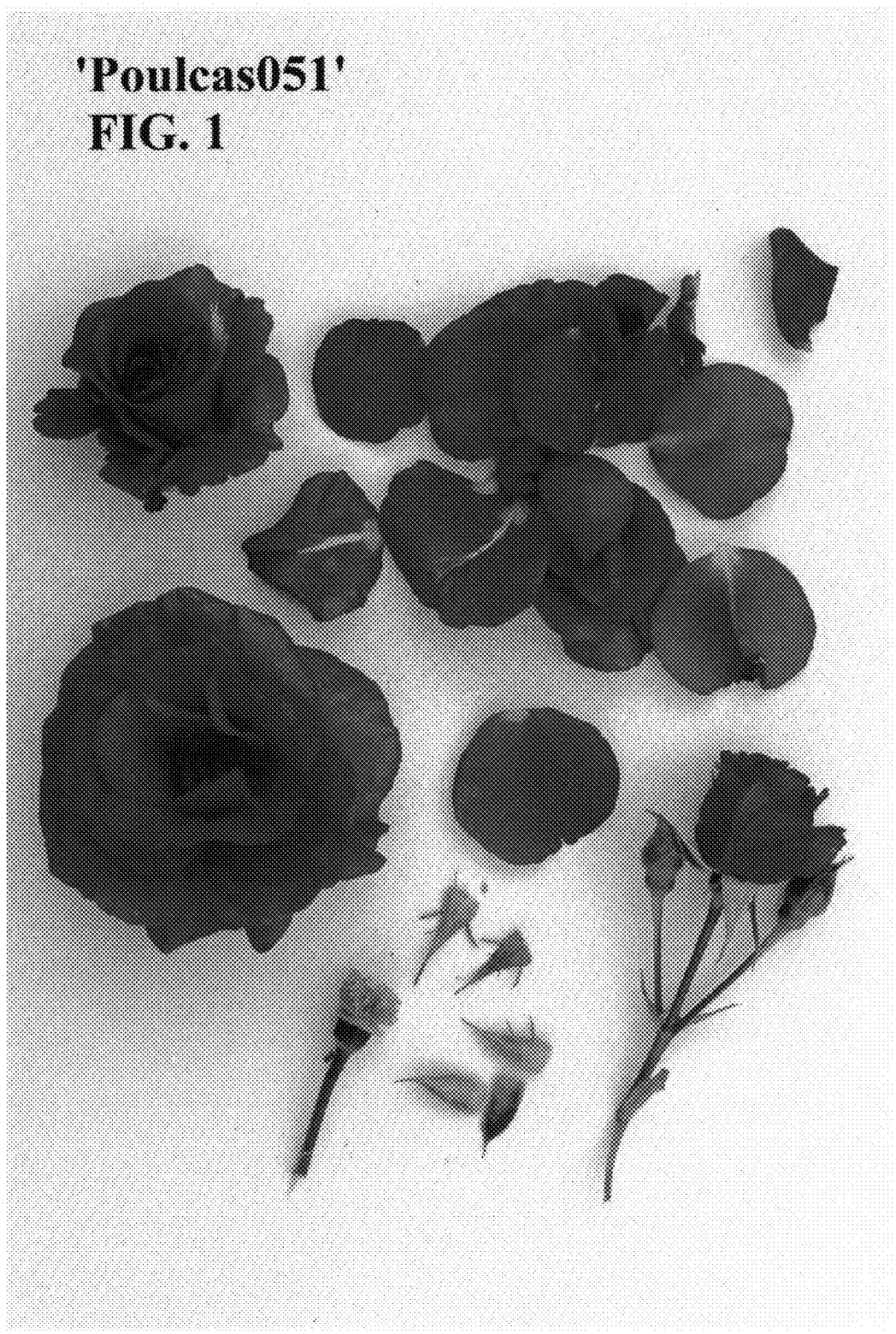
Figure 2:
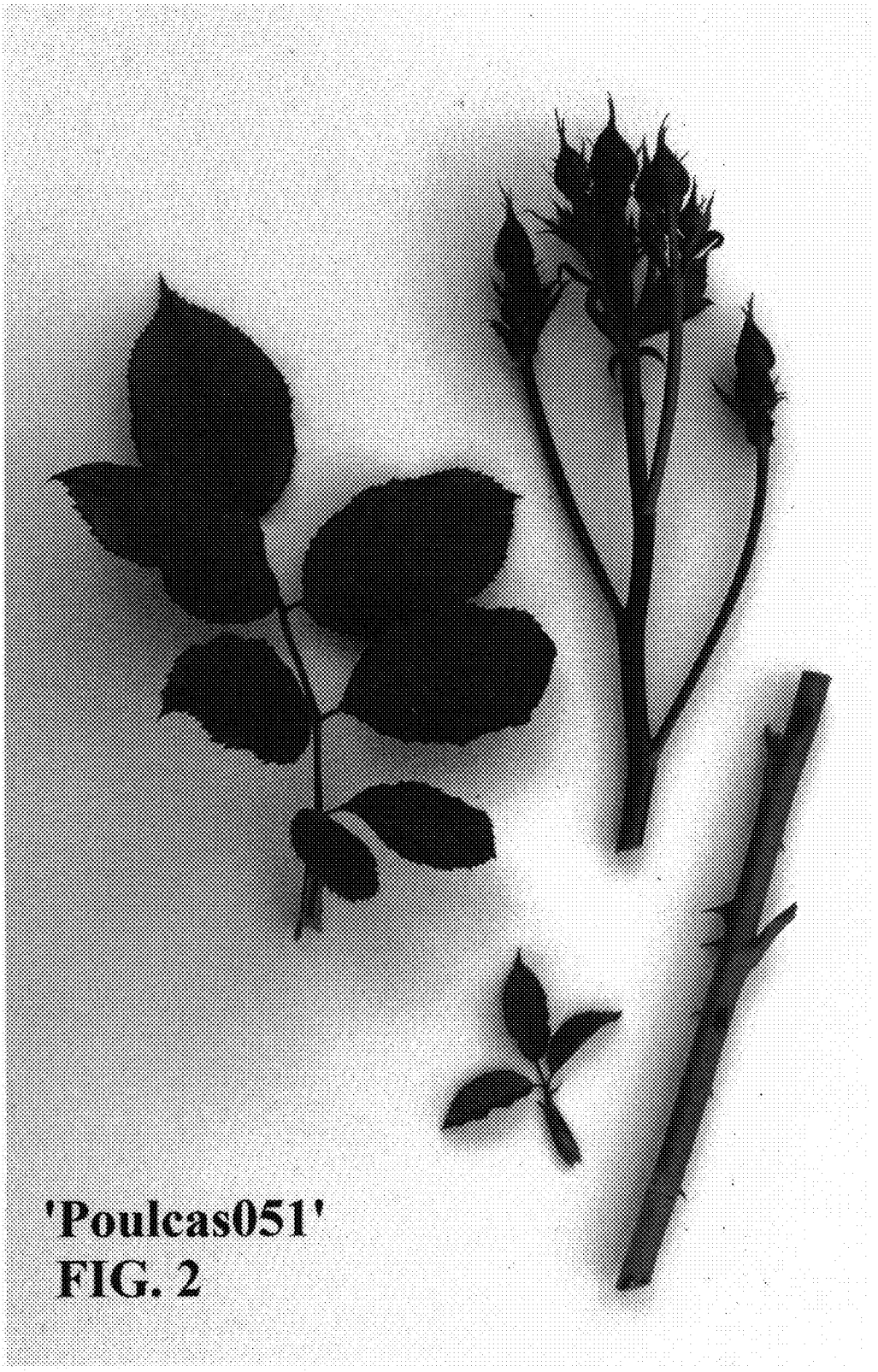

Specifically illustrated in FIG. 2 of the drawings are leaves stems and a cluster of flower buds. Plants shown are 2 years of age.

DETAILED DESCRIPTION OF THE VARIETY

The following is a description of 'Poulcas051', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas034', U.S. Plant Pat. No. 24,225 are compared to 'Poulcas051' in Chart 1.

CHART 1

| | 'Poulcas051' | 'Poulcas034' |
|---|---|---|
| Petal Count | 45 | 70 |
| Flower Diameter | 95 mm | 90 to 100 mm |
| General Tonality of Flower Color | Red Group 53B to Red Group 53C | Red Group 45B |

Flower and flower bud:

*Blooming habit.*—Continuous.

*Flower bud.*—Size: Upon opening, 26 mm in length from base of receptacle to end of bud. Bud diameter is 15 mm. Bud form: Ovoid. Bud color: As sepals divide petals are Red Group 46A. Sepal inner surface: Color: Yellow-Green Group 146D. Surface: Lightly pubescent. Sepal outer surface: Color: Yellow-Green Group 144A. Texture: Smooth. Sepal Shape: Apex: Cirrhose. Base: Flat at union with receptacle. Sepal Margin: Margins have moderate foliaceous appendages on three of the five sepals. Sepal size: 25 mm long, 8 mm wide. Receptacle: Texture: Smooth. Size: 5 mm in height, 9 mm wide. Color: Yellow-Green Group 144A with intonations of Greyed-Red Group 180B. Shape: Campanulate. Pedicel: Surface: Smooth. Length: 35 mm. Diameter: 3 mm on average. Color: Yellow-Green Group 144B with intonations of Greyed-Red Group 180A. Strength: Strong. Peduncle: Length: About 10 cm. Diameter: About 4 mm. Color: Yellow-Green Group 144A with intonations of Greyed-Red Group 181A. Texture: Smooth.

*Flower bud development.*—Flower buds are borne in clusters of 5 to 9 flower buds per stem.

*Flower bloom.*—Fragrance: Moderate perfume scent. Duration: The blooms have a duration on the plant of approximately 10 days. Petals fall cleanly away from plant after flowers have fully matured. Size: Flower diameter is 95 mm when open. Flower depth is 40 mm. Flower shape: High centered, double, with a high pointed center which is tightly closed. Shape of flower, side view: The upper portion is flat. The lower portion is flat.

*Petalage.*—Under normal conditions, flowers have about 30 petals.

*General tonality of flower.*—Open flowers are Red Group 53B to Red Group 53C. Becoming Red-Purple Group 58B as flowers age.

*Petal color.*—Upon opening, and after opening, Upper surface: Red Group 53B. Basal zone intonations of Orange-Red Group 32C. Lower surface: Red Group 53C. Basal petal spots: Upper surface: Yellow Group 9B about 3 mm long and 5 mm wide. Lower surface: Yellow Group 9B about 3 mm long and 4 mm wide.

*Petals.*—Petal Reflex: Somewhat reflexed. Margin: Mostly entire and uniform. Some petals have a small cleft at the margin. Outer petals have strong undulations, while inner petals have moderate undulations. Shape: Generally rounded. Apex shape: Rounded. Base shape: Rounded. Size: 40 mm (l)×40 mm (w). Texture: Smooth. Thickness: Average.

*Petaloids.*—Size: 20 mm (l) by 12 mm (w). Quantity: About 10. Shape: Elliptical with an acute base and acute apex. Color:

*Reproductive flower parts.*—Pollen: None observed. Anthers: Size: 3 mm in length. Color: Yellow 12A. Quantity: 45 on average. Filaments: Color: Yellow-Orange Group 21C. Length: 7 mm. Pistils: Length: 4 mm. Quantity: 35 on average. Stigmas: Color: Greyed-Yellow Group 160A. Styles: Color: Red Group 52D. Location of stigmas: Inferior in location relative to the length of the filaments and the height of the anthers. Hips: None Observed.

Plant:

*Plant growth.*—Compact shrub. Upright, bushy. Plants are 65 cm in height, and 55 cm wide.

*Stems.*—Color of juvenile growth: Yellow-Green Group 144B. Color of mature growth: Yellow-Green Group 144A. Length: Canes are about 40 cm from the base of the plant to the flowering portion. Diameter: About 9 mm. Internodes: On mature canes about 53 mm between nodes. Surface Texture: Young wood: Smooth. Older wood: Smooth.

*Long prickles.*—Incidence: 5 prickles per 10 cm of stem. Size: Average length of prickles on mature stems is 5 mm. Shape: Upper portion is linear. Lower portion is concave. Color: Juvenile prickles: Greyed-Red Group 180A. Mature prickles: Greyed-Red Group 180A.

*Plant foliage.*—Compound leaf: 170 mm (l)×120 (w). Quantity: 2 leaves per 10 cm of stem on average. Leaf bearing angle to the stem: 45 degrees. Color of juvenile foliage: Upper side: Yellow-Green Group 144A with intonations of Greyed-Red Group 182A. Lower side: Yellow-Green Group 144B with intonations of Greyed-Red Group 182A. Color of mature foliage: Upper side: Yellow-Green Group 147A. Lower side: Yellow-Green Group 146B.

*Plant leaves and leaflets.*—Stipules: Size: 20 mm long, 6 mm wide. Quantity: 2 per compound leaf. Shape: Linear, slightly broad based with outward extending apices. Margins: Finely serrated. Color: Yellow-Green Group 144B. Petiole: Length: 30 mm. Diameter: 2 mm. Upper surface color: Yellow-Green Group 144A with intonations of Greyed-Red Group 182A. Lower surface color: Yellow-Green Group 144A. Rachis: Length: 70 mm. Upper surface color: Yellow-Green Group 144A with intonations of Greyed-Red Group 182A. Lower surface color: Yellow-Green Group 144A. Leaflet: Quantity: Normally 7 leaflets. Margins: Serrated. Size: Terminal leaflets are about 63 mm long, 40 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

*Disease resistance.*—Above average resistance to powdery mildew *Sphaerotheca pannosa,* downy mildew *Peronospora sparsa,* rust *Phragmidium* sps., black spot *Diplocarpon rosae,* and *Botrytis cinerea* under normal growing conditions.

*Cold hardiness.*—The variety is tolerant to USDA Cold Hardiness Zone 6.

*Heat tolerance.*—The variety has been found to be suitable for climate conditions found in the American Horticulture Society heat zone 7.

I claim:

1. A new and distinct variety of rose plant of the Floribunda rose class named 'Poulcas051', substantially as illustrated and described herein, due to its abundant red flowers, disease resistance, and extended period of bloom.

* * * * *

'Poulcas051'

'Poulcas051'